(12) United States Patent
Thornton

(10) Patent No.: US 7,081,131 B2
(45) Date of Patent: *Jul. 25, 2006

(54) ARTIFICIAL VALVE

(75) Inventor: Sally C. Thornton, Marlborough, MA (US)

(73) Assignee: Boston Scientific Corporation, Natick, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/873,052

(22) Filed: Jun. 22, 2004

(65) Prior Publication Data

US 2004/0230297 A1  Nov. 18, 2004

Related U.S. Application Data

(63) Continuation of application No. 10/115,557, filed on Apr. 3, 2002, now Pat. No. 6,752,828.

(51) Int. Cl.
*A61F 2/06* (2006.01)

(52) U.S. Cl. .................. 623/1.24; 623/1.23; 623/2.12; 623/23.68

(58) Field of Classification Search ............... 623/1.24, 623/1.25, 1.26, 2.12, 2.13, 2.15, 2.16, 23.68, 623/1.23

See application file for complete search history.

(56) References Cited

U.S. PATENT DOCUMENTS

| | | | |
|---|---|---|---|
| 3,859,392 A | 1/1975 | Beermann et al. | 260/943 |
| 3,903,548 A | 9/1975 | Nakib | 3/1.5 |
| 4,218,782 A | 8/1980 | Rygg | 3/1.5 |
| 4,406,022 A | 9/1983 | Roy | 3/1.8 |
| 4,580,568 A | 4/1986 | Gianturco | 128/345 |
| 4,643,732 A | 2/1987 | Pietsch et al. | 632/2 |
| 4,851,001 A | 7/1989 | Taheri | 623/2 |
| 4,863,467 A | 9/1989 | Bokros | 623/2 |
| 5,024,232 A * | 6/1991 | Smid et al. | 600/431 |
| 5,032,128 A | 7/1991 | Alonso | 623/2 |
| 5,080,668 A | 1/1992 | Bolz et al. | 623/2 |
| 5,147,389 A | 9/1992 | Lane | 623/2 |
| 5,156,619 A | 10/1992 | Ehrenfeld | 623/1 |
| 5,163,953 A | 11/1992 | Vince | 623/2 |
| 5,358,518 A | 10/1994 | Camilli | 623/2 |
| 5,360,401 A | 11/1994 | Turnland | 604/96 |
| 5,413,599 A | 5/1995 | Imachi et al. | 623/2 |
| 5,476,471 A | 12/1995 | Shifrin et al. | 606/151 |
| 5,607,465 A | 3/1997 | Camilli | 623/1 |
| 5,609,598 A | 3/1997 | Laufer et al. | 606/142 |
| 5,769,780 A | 6/1998 | Hata et al. | 600/36 |
| 5,810,847 A | 9/1998 | Laufer et al. | 606/142 |
| 5,855,601 A | 1/1999 | Bessler et al. | 623/2 |
| 5,919,224 A | 7/1999 | Thompson et al. | 623/1 |
| 6,015,431 A | 1/2000 | Thornton et al. | 623/1 |
| 6,027,525 A | 2/2000 | Suh et al. | 623/1 |
| 6,110,201 A | 8/2000 | Quijano et al. | 623/2.1 |

(Continued)

FOREIGN PATENT DOCUMENTS

EP  0732087  9/1996

(Continued)

*Primary Examiner*—Corrine McDermott
*Assistant Examiner*—Thomas J. Sweet
(74) *Attorney, Agent, or Firm*—Brooks & Cameron, PLLC

(57) ABSTRACT

Method and apparatus implementing and using techniques for controlling flow in a body lumen, including use of an implantable medical device. The device includes a membrane implantable in a body lumen and invertibly deformable between a first position and a second position. The membrane is invertible in response to the direction of fluid flow through the lumen and can be deformable by fluid flow in the body lumen.

19 Claims, 14 Drawing Sheets

U.S. PATENT DOCUMENTS

| | | | | |
|---|---|---|---|---|
| 6,126,686 A | 10/2000 | Badylak et al. | | 623/1.24 |
| 6,162,245 A | 12/2000 | Jayaraman | | 623/1.15 |
| 6,168,614 B1 | 1/2001 | Andersen et al. | | 623/1 |
| 6,168,619 B1 | 1/2001 | Dinh et al. | | 623/1.13 |
| 6,200,336 B1 | 3/2001 | Pavenik et al. | | 623/1.15 |
| 6,241,763 B1 | 6/2001 | Drasler et al. | | 623/1.24 |
| 6,287,334 B1 | 9/2001 | Moll et al. | | 623/1.24 |
| 6,299,637 B1 | 10/2001 | Shaolian et al. | | 623/1.24 |
| 6,315,793 B1 | 11/2001 | Bokros et al. | | 623/1.24 |
| 6,319,281 B1 | 11/2001 | Patel | | 623/2.3 |
| 6,328,727 B1 | 12/2001 | Frazier et al. | | 604/500 |
| 6,334,873 B1 | 1/2002 | Lane et al. | | 623/2.14 |
| 6,440,164 B1 | 8/2002 | DiMatteo et al. | | 623/1.24 |
| 6,458,153 B1 | 10/2002 | Bailey et al. | | 623/1.24 |
| 6,503,272 B1 | 1/2003 | Duerig et al. | | 623/1.24 |
| 6,508,833 B1 | 1/2003 | Pavenik et al. | | 623/1.15 |
| 6,572,652 B1 | 6/2003 | Shaknovich | | 623/2.11 |
| 6,602,286 B1 | 8/2003 | Strecker | | 623/1.24 |
| 6,666,885 B1 | 12/2003 | Moe | | 623/2.12 |
| 6,666,886 B1 | 12/2003 | Tranquillo et al. | | 623/2.42 |
| 6,669,725 B1 | 12/2003 | Scott | | 623/2.36 |
| 6,673,109 B1 | 1/2004 | Cox | | 623/2.12 |
| 6,676,698 B1 | 1/2004 | McGuckin, Jr. et al. | | 623/1.24 |
| 6,676,702 B1 | 1/2004 | Mathis | | 623/2.36 |
| 6,682,558 B1 | 1/2004 | Tu et al. | | 623/2.11 |
| 6,682,559 B1 | 1/2004 | Myers et al. | | 623/2.13 |
| 6,685,739 B1 | 2/2004 | DiMatteo et al. | | 623/1.24 |
| 6,692,512 B1 | 2/2004 | Jang | | 606/200 |
| 6,695,866 B1 | 2/2004 | Kuehn et al. | | 606/213 |
| 6,695,878 B1 | 2/2004 | McGuckin, Jr. et al. | | 623/1.19 |
| 6,709,456 B1 | 3/2004 | Langberg et al. | | 623/2.37 |
| 6,709,457 B1 | 3/2004 | Otte et al. | | 623/2.4 |
| 6,716,241 B1 | 4/2004 | Wilder et al. | | 623/1.24 |
| 6,716,244 B1 | 4/2004 | Klaco | | 623/2.4 |
| 6,719,767 B1 | 4/2004 | Kimblad | | 606/142 |
| 6,719,784 B1 | 4/2004 | Henderson | | 623/1.44 |
| 6,719,786 B1 | 4/2004 | Ryan et al. | | 623/2.11 |
| 6,719,787 B1 | 4/2004 | Cox | | 623/2.12 |
| 6,719,788 B1 | 4/2004 | Cox | | 623/2.12 |
| 6,719,789 B1 | 4/2004 | Cox | | 623/2.13 |
| 6,719,790 B1 | 4/2004 | Brendzel et al. | | 623/2.4 |
| 6,723,038 B1 | 4/2004 | Schroeder et al. | | 600/16 |
| 6,723,122 B1 | 4/2004 | Yang et al. | | 623/2.1 |
| 6,723,123 B1 | 4/2004 | Kazatchkov et al. | | 623/2.2 |
| 6,726,715 B1 | 4/2004 | Sutherland | | 623/2.1 |
| 6,726,716 B1 | 4/2004 | Marquez | | 623/2.36 |
| 6,726,717 B1 | 4/2004 | Alfieri et al. | | 623/2.36 |
| 6,730,118 B1 | 5/2004 | Spenser et al. | | 623/1.24 |
| 6,730,121 B1 | 5/2004 | Ortiz et al. | | 623/2.17 |
| 6,730,122 B1 | 5/2004 | Pan et al. | | 623/2.33 |
| 6,736,845 B1 | 5/2004 | Marquez et al. | | 623/2.11 |
| 6,736,846 B1 | 5/2004 | Cox | | 623/2.12 |
| 6,749,630 B1 | 6/2004 | McCarthy et al. | | 623/2.36 |
| 6,752,813 B1 | 6/2004 | Goldfarb et al. | | 606/139 |
| 6,752,828 B1 | 6/2004 | Thornton | | 623/1.24 |
| 6,755,857 B1 | 6/2004 | Peterson et al. | | 623/2.17 |
| 6,761,734 B1 | 7/2004 | Suhr | | 623/1.35 |
| 6,761,735 B1 | 7/2004 | Eberhardt et al. | | 623/2.1 |
| 6,764,494 B1 | 7/2004 | Menz et al. | | 606/159 |
| 6,764,508 B1 | 7/2004 | Roehe et al. | | 623/2.11 |
| 6,764,509 B1 | 7/2004 | Chinn et al. | | 623/2.12 |
| 6,764,510 B1 | 7/2004 | Vidlund et al. | | 623/2.34 |
| 6,767,362 B1 | 7/2004 | Schreck | | 623/2.11 |
| 6,769,434 B1 | 8/2004 | Liddicoat et al. | | 128/898 |
| 6,770,083 B1 | 8/2004 | Seguin | | 606/142 |
| 6,780,200 B1 | 8/2004 | Jansen | | 623/2.17 |
| 6,786,924 B1 | 9/2004 | Ryan et al. | | 623/2.36 |
| 6,786,925 B1 | 9/2004 | Schoon et al. | | 623/2.38 |
| 6,790,229 B1 | 9/2004 | Berreklouw | | 623/2.1 |
| 6,790,230 B1 | 9/2004 | Beyersdorf et al. | | 623/2.18 |
| 6,790,231 B1 | 9/2004 | Liddicoat et al. | | 623/2.37 |
| 6,793,673 B1 | 9/2004 | Kowalsky et al. | | 623/2.36 |
| 6,797,000 B1 | 9/2004 | Simpson et al. | | 623/2.15 |
| 6,797,001 B1 | 9/2004 | Mathis et al. | | 623/2.37 |
| 6,797,002 B1 | 9/2004 | Spence et al. | | 623/2.38 |
| 6,802,860 B1 | 10/2004 | Cosgrove et al. | | 623/2.11 |
| 6,805,710 B1 | 10/2004 | Bolling et al. | | 623/2.36 |
| 6,805,711 B1 | 10/2004 | Quijano et al. | | 623/2.37 |
| 6,810,882 B1 | 11/2004 | Langberg et al. | | 128/898 |
| 6,821,297 B1 | 11/2004 | Snyders | | 623/2.18 |
| 6,824,562 B1 | 11/2004 | Mathis et al. | | 623/2.36 |
| 6,830,584 B1 | 12/2004 | Seguin | | 623/2.11 |
| 6,830,585 B1 | 12/2004 | Artof et al. | | 623/2.11 |
| 6,837,902 B1 | 1/2005 | Nguyen et al. | | 623/2.13 |
| 6,840,246 B1 | 1/2005 | Downing | | 128/898 |
| 6,840,957 B1 | 1/2005 | DiMatteo et al. | | 623/1.24 |
| 6,846,324 B1 | 1/2005 | Stobie | | 623/2.11 |
| 6,846,325 B1 | 1/2005 | Liddicoat | | 623/2.4 |
| 6,858,039 B1 | 2/2005 | McCarthy | | 623/2.36 |
| 2001/0021872 A1 | 9/2001 | Bailey et al. | | 623/1.24 |
| 2001/0039450 A1 | 11/2001 | Pavenik et al. | | 623/1.24 |
| 2002/0052651 A1* | 5/2002 | Myers et al. | | 623/2.15 |
| 2003/0023300 A1 | 1/2003 | Bailey et al. | | 623/1.13 |
| 2003/0069635 A1 | 4/2003 | Cartledge et al. | | 623/2.13 |
| 2003/0069646 A1 | 4/2003 | Stinson | | 623/23.7 |
| 2003/0130726 A1 | 7/2003 | Thorpe et al. | | 623/1.24 |
| 2003/0130729 A1 | 7/2003 | Paniagua et al. | | 623/2.11 |
| 2003/0229394 A1 | 12/2003 | Ogle et al. | | 623/2.14 |
| 2003/0229395 A1 | 12/2003 | Cox | | 623/2.36 |
| 2003/0233142 A1 | 12/2003 | Morales et al. | | 623/2.37 |
| 2003/0236568 A1 | 12/2003 | Hojeibane et al. | | 623/1.24 |
| 2003/0236569 A1 | 12/2003 | Mathis et al. | | 623/1.26 |
| 2004/0002719 A1 | 1/2004 | Oz et al. | | 606/142 |
| 2004/0003819 A1 | 1/2004 | St. Goar et al. | | 128/898 |
| 2004/0010305 A1 | 1/2004 | Alferness et al. | | 623/1.11 |
| 2004/0015230 A1 | 1/2004 | Moll et al. | | 623/1.24 |
| 2004/0015232 A1 | 1/2004 | Shu et al. | | 623/2.4 |
| 2004/0015233 A1 | 1/2004 | Jansen | | 623/2.18 |
| 2004/0019374 A1 | 1/2004 | Hojeibane et al. | | 623/1.13 |
| 2004/0019377 A1 | 1/2004 | Taylor et al. | | 623/2.11 |
| 2004/0019378 A1 | 1/2004 | Hlavka et al. | | 623/2.11 |
| 2004/0024447 A1 | 2/2004 | Haverich | | 623/1.24 |
| 2004/0024451 A1 | 2/2004 | Johnson et al. | | 623/2.11 |
| 2004/0024452 A1 | 2/2004 | Kruse et al. | | 623/2.13 |
| 2004/0030321 A1 | 2/2004 | Fangrow, Jr. | | 604/533 |
| 2004/0030381 A1 | 2/2004 | Shu | | 623/2.11 |
| 2004/0030382 A1 | 2/2004 | St. Goar et al. | | 623/2.36 |
| 2004/0030405 A1 | 2/2004 | Carpentier et al. | | 623/23.72 |
| 2004/0034380 A1 | 2/2004 | Woolfson et al. | | 606/170 |
| 2004/0034411 A1 | 2/2004 | Quijano et al. | | 623/2.11 |
| 2004/0039436 A1 | 2/2004 | Spenser et al. | | 623/1.13 |
| 2004/0039442 A1 | 2/2004 | St. Goar et al. | | 623/2.36 |
| 2004/0039443 A1 | 2/2004 | Solem et al. | | 623/2.37 |
| 2004/0044350 A1 | 3/2004 | Martin et al. | | 606/139 |
| 2004/0044365 A1 | 3/2004 | Bachman | | 606/213 |
| 2004/0044403 A1 | 3/2004 | Bischoff et al. | | 623/1.41 |
| 2004/0049207 A1 | 3/2004 | Goldfarb et al. | | 606/139 |
| 2004/0049211 A1 | 3/2004 | Tremulis et al. | | 606/153 |
| 2004/0049266 A1 | 3/2004 | Anduiza et al. | | 623/2.11 |
| 2004/0059351 A1 | 3/2004 | Eigler et al. | | 606/148 |
| 2004/0059411 A1 | 3/2004 | Strecker | | 623/1.23 |
| 2004/0059412 A1 | 3/2004 | Lytle, IV et al. | | 623/2.11 |
| 2004/0060161 A1 | 4/2004 | Leal et al. | | 29/558 |
| 2004/0073301 A1 | 4/2004 | Donlon et al. | | 623/2.11 |
| 2004/0073302 A1 | 4/2004 | Rourke et al. | | 623/2.36 |
| 2004/0078072 A1 | 4/2004 | Tu et al. | | 623/1.23 |
| 2004/0078074 A1 | 4/2004 | Anderson et al. | | 623/2.11 |
| 2004/0082910 A1 | 4/2004 | Constantz et al. | | 604/101.04 |
| 2004/0082923 A1 | 4/2004 | Field | | 604/267 |
| 2004/0082991 A1 | 4/2004 | Nguyen et al. | | 623/2.14 |
| 2004/0087975 A1 | 5/2004 | Lucatero et al. | | 606/139 |
| 2004/0088045 A1 | 5/2004 | Cox | | 623/2.13 |
| 2004/0088046 A1 | 5/2004 | Speziali | | 623/2.19 |
| 2004/0092858 A1 | 5/2004 | Wilson et al. | | 604/9 |

2004/0093060 A1 5/2004 Seguin et al. .............. 623/1.11
2004/0093070 A1 5/2004 Hojeibane et al. ......... 623/1.15
2004/0093080 A1 5/2004 Helmus et al. ............ 623/2.41
2004/0097979 A1 5/2004 Svanidze et al. ........... 606/151
2004/0098098 A1 5/2004 McGuckin, Jr. et al. ... 623/1.14
2004/0098112 A1 5/2004 DiMatteo et al. .......... 623/1.24
2004/0102839 A1 5/2004 Cohn et al. ................ 623/2.11
2004/0102840 A1 5/2004 Solem et al. ............. 623/2.11
2004/0102842 A1 5/2004 Jansen ....................... 623/2.38
2004/0106976 A1 6/2004 Bailey et al. .............. 623/1.11
2004/0106990 A1 6/2004 Spence et al. ............. 623/2.11
2004/0106991 A1 6/2004 Hopkins et al. ........... 623/2.13
2004/0111096 A1 6/2004 Tu et al. ..................... 606/108
2004/0117009 A1 6/2004 Cali et al. .................. 623/2.12
2004/0122448 A1 6/2004 Levine ....................... 606/139
2004/0122512 A1 6/2004 Navia et al. ............... 623/2.12
2004/0122513 A1 6/2004 Navia et al. ............... 623/2.12
2004/0122514 A1 6/2004 Fogarty et al. ............ 623/2.14
2004/0122515 A1 6/2004 Chu .......................... 623/2.29
2004/0122516 A1 6/2004 Fogarty et al. ............ 623/2.37
2004/0127979 A1 7/2004 Wilson et al. ............... 623/2.1
2004/0127980 A1 7/2004 Kowalsky et al. ......... 623/2.11
2004/0127981 A1 7/2004 Rahdert et al. ............ 623/2.36
2004/0127982 A1 7/2004 Machold et al. ........... 623/2.36
2004/0133220 A1 7/2004 Lashinski et al. ........... 606/151
2004/0133267 A1 7/2004 Lane ......................... 623/1.24
2004/0133273 A1 7/2004 Cox .......................... 623/2.11
2004/0138742 A1 7/2004 Myers et al. .............. 623/2.12
2004/0138743 A1 7/2004 Myers et al. .............. 623/2.12
2004/0138744 A1 7/2004 Lashinski et al. .......... 623/2.36
2004/0138745 A1 7/2004 Macoviak et al. ......... 623/2.36
2004/0148018 A1 7/2004 Carpentier et al. ........ 623/2.18
2004/0148019 A1 7/2004 Vidlund et al. ............ 623/2.36
2004/0148020 A1 7/2004 Vidlund et al. ............ 623/2.36
2004/0153052 A1 8/2004 Mathis .......................... 606/1
2004/0153146 A1 8/2004 Lashinski et al. .......... 623/2.36
2004/0153147 A1 8/2004 Mathis ...................... 623/2.37
2004/0158321 A1 8/2004 Reuter et al. .............. 623/2.36
2004/0162610 A1 8/2004 Liska et al. ................ 623/2.11
2004/0167539 A1 8/2004 Keuhn et al. ............... 606/108
2004/0167620 A1 8/2004 Ortiz et al. ................ 623/2.11
2004/0172046 A1 9/2004 Hlavka et al. .............. 606/142
2004/0176839 A1 9/2004 Huynh et al. ................ 623/2.4
2004/0176840 A1 9/2004 Langberg et al. .......... 623/2.37
2004/0181238 A1 9/2004 Zarbatany et al. .......... 606/108
2004/0186444 A1 9/2004 Daly et al. .................. 604/247
2004/0186558 A1 9/2004 Pavcnik et al. ............ 623/1.24
2004/0186561 A1 9/2004 McGuckin, Jr. et al. ... 623/1.36
2004/0186563 A1 9/2004 Iobbi ......................... 623/2.11
2004/0186565 A1 9/2004 Schreck ..................... 623/2.18
2004/0186566 A1 9/2004 Hindrichs et al. ......... 623/2.37
2004/0193191 A1 9/2004 Starksen et al. ............ 606/153
2004/0193253 A1 9/2004 Thorpe et al. ............. 623/1.24
2004/0193260 A1 9/2004 Alferness et al. .......... 623/2.11
2004/0199155 A1 10/2004 Mollenauer .................. 606/27
2004/0199183 A1 10/2004 Oz et al. .................... 606/142
2004/0199191 A1 10/2004 Schwartz .................... 606/159
2004/0204758 A1 10/2004 Eberhardt et al. ......... 623/2.15
2004/0206363 A1 10/2004 McCarthy et al. .......... 128/898
2004/0210240 A1 10/2004 Saint .......................... 606/139
2004/0210301 A1 10/2004 Obermiller ................. 623/1.24
2004/0210303 A1 10/2004 Sedransk .................... 623/2.1
2004/0210304 A1 10/2004 Seguin et al. .............. 623/2.11
2004/0210305 A1 10/2004 Shu et al. .................. 623/2.11
2004/0210306 A1 10/2004 Quijano et al. ............ 623/2.17
2004/0210307 A1 10/2004 Khairkhahan .............. 623/2.18
2004/0215333 A1 10/2004 Duran et al. ............... 623/1.24
2004/0215339 A1 10/2004 Drasler et al. ............... 623/3.1
2004/0220654 A1 11/2004 Mathis et al. .............. 623/1.11
2004/0220657 A1 11/2004 Nieminen et al. ......... 623/1.15
2004/0225322 A1 11/2004 Garrison et al. ............ 606/200
2004/0225344 A1 11/2004 Hoffa et al. ................. 623/1.1
2004/0225348 A1 11/2004 Case et al. ................. 623/1.15
2004/0225352 A1 11/2004 Osborne et al. ........... 623/1.24
2004/0225353 A1 11/2004 McGuckin, Jr. et al. ... 623/2.11
2004/0225354 A1 11/2004 Allen et al. ................ 623/2.11
2004/0225355 A1 11/2004 Stevens ..................... 623/2.11
2004/0225356 A1 11/2004 Frater ........................ 623/2.14
2004/0230117 A1 11/2004 Tosaya et al. .............. 600/439
2004/0230297 A1 11/2004 Thornton ................... 623/1.24
2004/0236411 A1 11/2004 Sarac et al. ................ 623/1.26
2004/0236418 A1 11/2004 Stevens ..................... 623/2.11
2004/0236419 A1 11/2004 Milo ......................... 623/2.36
2004/0243153 A1 12/2004 Liddicoat et al. ........... 606/151
2004/0243219 A1 12/2004 Fischer et al. ............. 623/1.15
2004/0243227 A1 12/2004 Starksen et al. ........... 623/2.11
2004/0243228 A1 12/2004 Kowalsky et al. ......... 623/2.11
2004/0243230 A1 12/2004 Navia et al. ............... 623/2.36
2004/0249452 A1 12/2004 Adams et al. ............. 623/2.36
2004/0254600 A1 12/2004 Zarbatany et al. .......... 606/194
2004/0254636 A1 12/2004 Flagle et al. ............... 623/1.24
2004/0260276 A1 12/2004 Rudko et al. ................. 606/15
2004/0260317 A1 12/2004 Bloom et al. ............... 606/151
2004/0260322 A1 12/2004 Rudko et al. ............... 606/167
2004/0260389 A1 12/2004 Case et al. ................. 623/1.24
2004/0260390 A1 12/2004 Sarac et al. ................ 623/1.24
2004/0260393 A1 12/2004 Rahdert et al. ............ 623/2.36
2004/0260394 A1 12/2004 Douk et al. ................ 623/2.36
2004/0267357 A1 12/2004 Allen et al. ................ 623/2.11
2005/0004583 A1 1/2005 Oz et al. .................... 606/142
2005/0004667 A1 1/2005 Swinford et al. .......... 623/2.36
2005/0010285 A1 1/2005 Lambrecht et al. ........ 623/2.18
2005/0010287 A1 1/2005 Macoviak et al. ......... 623/2.36
2005/0015112 A1 1/2005 Cohn et al. ................. 606/200
2005/0021056 A1 1/2005 St. Goar et al. ............ 606/144
2005/0021136 A1 1/2005 Xie et al. .................. 623/2.14
2005/0027261 A1 2/2005 Weaver et al. .............. 604/246
2005/0027348 A1 2/2005 Case et al. ................. 623/1.24
2005/0027351 A1 2/2005 Reuter et al. .............. 623/2.11
2005/0027353 A1 2/2005 Alferness et al. .......... 623/2.11
2005/0033398 A1 2/2005 Seguin ...................... 623/1.11
2005/0033419 A1 2/2005 Alferness et al. .......... 623/2.11
2005/0033446 A1 2/2005 Deem et al. ............... 623/23.6
2005/0038506 A1 2/2005 Webler et al. ............. 623/2.11
2005/0038507 A1 2/2005 Alferness et al. .......... 623/2.11
2005/0043790 A1 2/2005 Seguin ...................... 623/2.18
2005/0043792 A1 2/2005 Solem et al. .............. 623/2.36

FOREIGN PATENT DOCUMENTS

EP 0856300 8/1998
FR 2728457 6/1996
WO WO 00/67679 11/2000
WO WO 01/19285 3/2001
WO WO 01/54625 8/2001
WO WO 01/56500 8/2001
WO WO 02/41764 5/2002
WO WO 2004/019825 3/2004
WO WO 2004/021893 3/2004
WO WO 2004/023980 3/2004
WO WO 2004/030568 4/2004
WO WO 2004/030569 4/2004
WO WO 2004/030570 4/2004
WO WO 2004/032724 4/2004
WO WO 2004/032796 4/2004
WO WO 2004/037128 5/2004
WO WO 2004/037317 5/2004
WO WO 2004/039432 5/2004
WO WO 2004/043265 5/2004
WO WO 2004/043273 5/2004
WO WO 2004/043293 5/2004
WO WO 2004/045370 6/2004
WO WO 2004/045378 6/2004
WO WO 2004/045463 6/2004
WO WO 2004/047677 6/2004
WO WO 2004/060217 7/2004

| | | | | | | |
|---|---|---|---|---|---|---|
| WO | WO 2004/060470 | 7/2004 | | WO | WO 2004/103222 | 12/2004 |
| WO | WO 2004/062725 | 7/2004 | | WO | WO 2004/103223 | 12/2004 |
| WO | WO 2004/066803 | 8/2004 | | WO | WO 2004/105584 | 12/2004 |
| WO | WO 2004/066826 | 8/2004 | | WO | WO 2004/105651 | 12/2004 |
| WO | WO 2004/069287 | 8/2004 | | WO | WO 2004/112582 | 12/2004 |
| WO | WO2004/075789 | 9/2004 | | WO | WO 2004/112585 | 12/2004 |
| WO | WO2004/080352 | 9/2004 | | WO | WO 2004/112643 | 12/2004 |
| WO | WO2004/082523 | 9/2004 | | WO | WO 2004/112652 | 12/2004 |
| WO | WO2004/082527 | 9/2004 | | WO | WO 2004/112657 | 12/2004 |
| WO | WO2004/082528 | 9/2004 | | WO | WO 2004/112658 | 12/2004 |
| WO | WO2004/082536 | 9/2004 | | WO | WO 2005/000152 | 1/2005 |
| WO | WO2004/082537 | 9/2004 | | WO | WO 2005/002424 | 1/2005 |
| WO | WO2004/082538 | 9/2004 | | WO | WO 2005/002466 | 1/2005 |
| WO | WO2004/082757 | 9/2004 | | WO | WO 2005/004753 | 1/2005 |
| WO | WO 2004/084746 | 10/2004 | | WO | WO 2005/007017 | 1/2005 |
| WO | WO 2004/084770 | 10/2004 | | WO | WO 2005/007018 | 1/2005 |
| WO | WO 2004/089246 | 10/2004 | | WO | WO 2005/007036 | 1/2005 |
| WO | WO 2004/089250 | 10/2004 | | WO | WO 2005/007037 | 1/2005 |
| WO | WO 2004/089253 | 10/2004 | | WO | WO 2005/009285 | 2/2005 |
| WO | WO 2004/091449 | 10/2004 | | WO | WO 2005/009286 | 2/2005 |
| WO | WO 2004/091454 | 10/2004 | | WO | WO 2005/009505 | 2/2005 |
| WO | WO 2004/093638 | 11/2004 | | WO | WO 2005/009506 | 2/2005 |
| WO | WO 2004/093726 | 11/2004 | | WO | WO 2005/011473 | 2/2005 |
| WO | WO 2004/093728 | 11/2004 | | WO | WO 2005/011534 | 2/2005 |
| WO | WO 2004/093730 | 11/2004 | | WO | WO 2005/011535 | 2/2005 |
| WO | WO 2004/093745 | 11/2004 | | WO | WO 2005/013860 | 2/2005 |
| WO | WO 2004/093935 | 11/2004 | | | | |
| WO | WO 2004/096100 | 11/2004 | | | | |

* cited by examiner

ARTIFICIAL VALVE

CROSS-REFERENCE TO RELATED APPLICATIONS

This application is a continuation of U.S. application Ser. No. 10/115,557, filed Apr. 3, 2002, now U.S. Pat. No. 6,752,828 issued Jun. 22, 2004, the specification of which is incorporated herein by reference.

FIELD OF THE INVENTION

This invention relates to medical devices for use in a body lumen.

BACKGROUND

A venous valve functions to prevent retrograde flow of blood and allow only antegrade flow of blood to the heart. Referring to FIG. 1A, a healthy venous valve 12 is illustrated in a vessel 10. The valve is bicuspid, with opposed cusps 14. In the closed condition, the cusps 14 are drawn together to prevent retrograde flow (arrow 16) of blood. Referring to FIG 1B, if the valve is incompetent, the cusps 14 do not seal properly and retrograde flow of blood occurs. Incompetence of a venous valve is thought to arise from at least the following two medical conditions: varicose veins and chronic venous insufficiency.

SUMMARY

This invention relates to medical devices for use with a body lumen. In one aspect, the invention features a medical device including a membrane implantable in a body lumen and invertibly deformable between a first position and a second position. The membrane is invertible in response to the direction of fluid flow through the lumen and can be deformable by fluid flow in the body lumen. The membrane can be invertible relative to a radial direction of the body lumen. The membrane can be reversibly deformable between the first position and the second position.

Implementations can include one or more of the following. The membrane can define a portion of a cone, and can include an anchoring element adjacent a vertex of the cone. The membrane can include an anchoring element configured to embed within the body lumen, or alternatively configured to penetrate through the body lumen. The anchoring element may be, for example, a loop or a barb. The membrane can be formed of a polymer, for example, a polyurethane, polyethylene or fluoroplastic.

In another aspect, the invention features a medical system. The system includes multiple membranes, each membrane implantable in a body lumen and invertibly deformable between a first position and a second position. Each membrane is invertible in response to the direction of fluid flow through the lumen.

Implementations of the system can include one or more of the following. The membranes can be symmetrically implantable in the body lumen. Each membrane can be invertible relative to a radial direction of the body lumen and can be deformable by fluid flow in the body lumen. At least one membrane can be reversibly deformable between the first position and the second position. At least one membrane can define a portion of a cone and can include an anchoring element adjacent a vertex of the cone. At least one membrane can include an anchoring element configured to embed within the body lumen or alternatively configured to penetrate through the body lumen. The anchoring element can be, for example, a loop or a barb. At least one membrane can be formed of a polymer, for example, a polyurethane, polyethylene or fluoroplastic.

In another aspect, the invention features a method. The method includes positioning at least one membrane in a body lumen, each membrane invertibly deformable between a first position and a second position. Each membrane is invertible in response to the direction of fluid flow through the lumen.

Implementations of the method can include one or more of the following. The method can include positioning multiple membranes in the body lumen. The multiple membranes can be positioned symmetrically in the body lumen. The method can include penetrating an anchoring element of the at least one membrane through the body lumen or, alternatively, embedding an anchoring element of the at least one membrane into the body lumen.

In another aspect, the invention features a method of controlling flow in a body lumen. The method includes invertibly deforming a membrane between a first position and a second position, the membrane being invertible in response to the direction of fluid flow through the lumen. Implementations can include one or more of the following. The membrane in the second position and a portion of the body lumen can define a cavity. Deformation of the membrane can be relative to a radial axis of the body lumen. The membrane can be deformable by fluid flow in the body lumen. The membrane in the first position and the membrane in the second position can be approximately mirror images of each other. The method can further include invertibly deforming a plurality of membranes.

Embodiments may have one or more of the following advantages. One or more invertible membranes, which can function as artificial valve cusps, can be implanted at a treatment site using a catheter. As such, implantation is minimally invasive and avoids surgery and the possibility of the inherent complications. The membrane is fabricated from a polymer such as a polyurethane, polyethylene or fluoroplastic, which materials are more easily accessible than a natural tissue excised from an animal, and can be manufactured with consistency and efficiency that could be more difficult or more expensive using a natural tissue.

Other features, objects, and advantages of the invention will be apparent from the description and drawings, and from the claims.

DETAILED DESCRIPTION

Figure 1A:
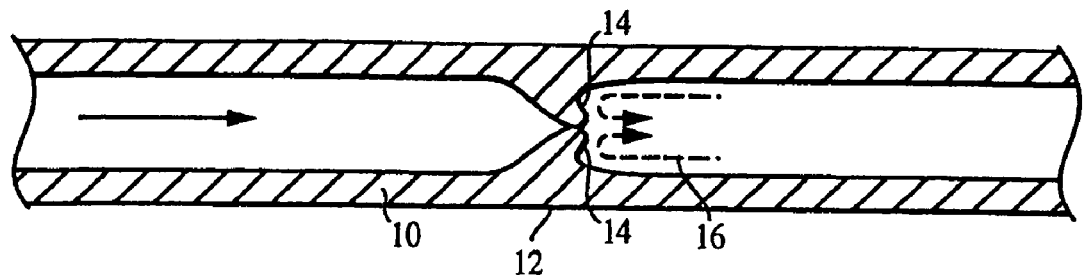
FIGS. 1A and 1B are illustrations of a venous valve and an incompetent venous valve, respectively.
Figure 1B:
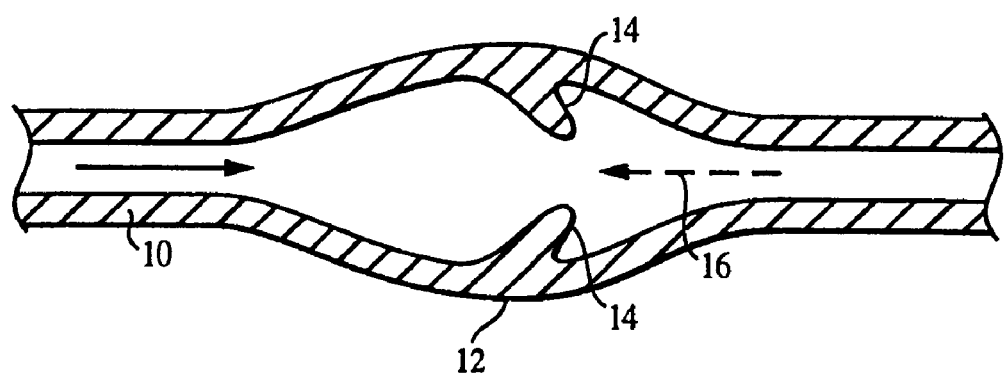

Referring to FIGS. 2A–2C through FIG. 4, a pair of artificial valve cusps 30 are illustrated positioned within a vessel 46, e.g., a vein. Cusps 30 can be positioned upstream or downstream relative to an incompetent venous valve, such as the valve shown in FIG. 1B. Each artificial valve cusp 30 includes at least one anchoring element 38 attached to an invertible portion 42, here, an approximately triangular, flexible membrane. Anchoring element 38 is generally configured to hold invertible portion 39 at a desired location in vessel 46. For example, anchoring element 38 can embed itself within a wall 44 of vessel 46, or penetrate through the wall to secure cusp 30 to the vessel. Invertible portion 42 is capable of deforming between a first position and a second position, e.g., between an opened condition and a closed position, in response to flow of body fluid in vessel 46 to allow or to reduce the flow in the vessel.

Figure 2C:
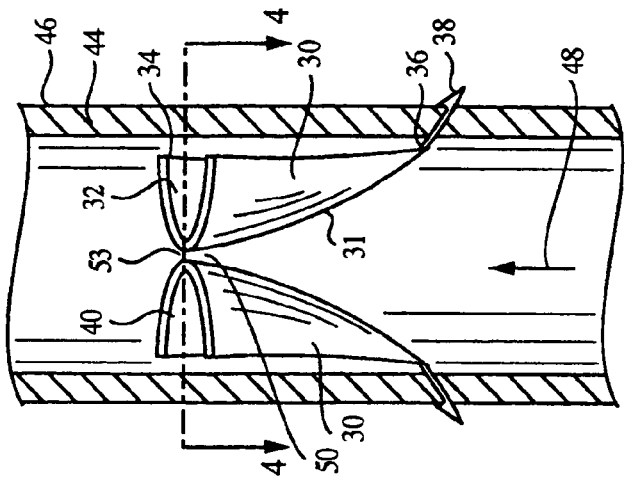
FIGS. 2A, 2B, and 2C are partial perspective views of an embodiment of a valve cusp.
Figure 2B:
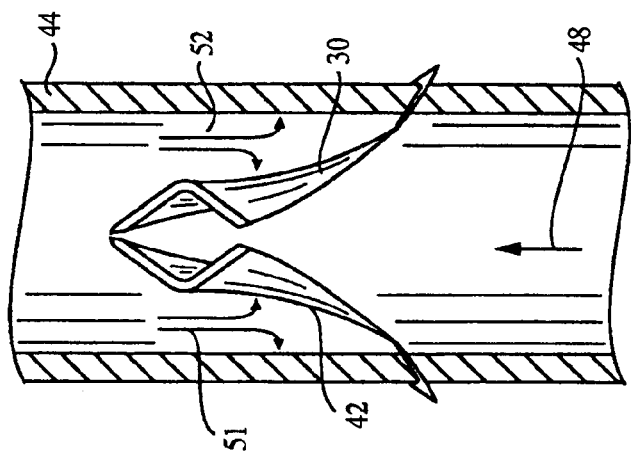
Figure 2A:
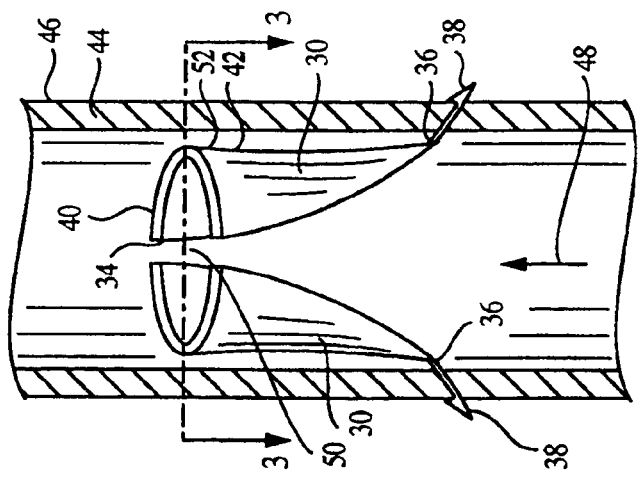
Figure 3:
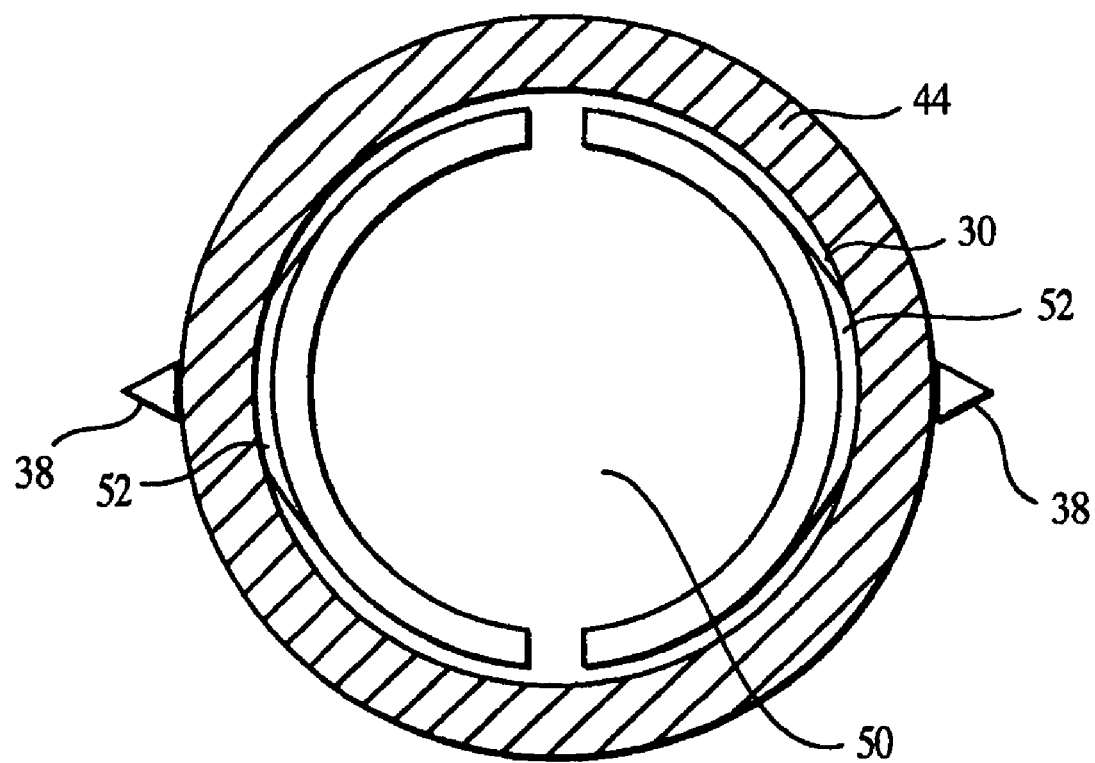
FIG. 3 is a cross-sectional view of the valve cusp of FIG. 2A, taken along line 3—3.

Referring particularly to FIG. 2A and FIG. 3, the cusps 30 are shown in a first position in which each cusp 30 forms an approximate semi-cone, such that an opening 50 is formed by the curved surfaces of the cusps 30. The opening 50 allows antegrade flow of a fluid through the vessel in the direction indicated by arrow 48. The membranes of invertible portions 42 are relatively thin and can conform closely to the vessel wall 44 to maximize the size of opening 50. However, each cusp 30 is also held slightly away from the wall 44 of the vessel 46 by the anchoring element 38, such that a gap 52 is formed between the invertible portion 42 and the wall 44.

Figure 4:
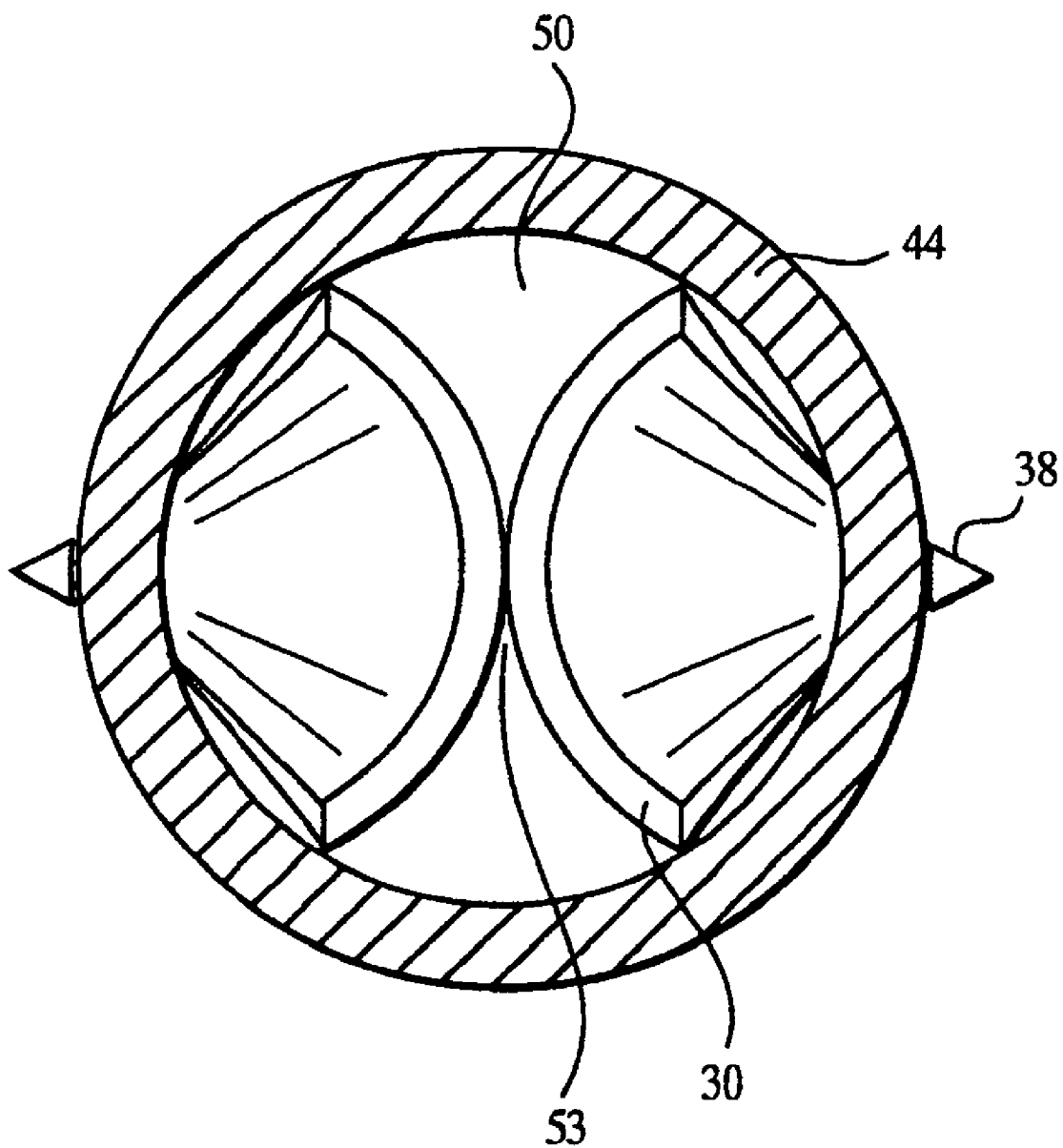
FIG. 4 is a cross-sectional view of the valve cusp of FIG. 2C, taken along line 4—4.

Referring particularly to FIG. 2B, retrograde flow of fluid (arrows 51) in the vessel can accumulate in the gap 52 and exert pressure on the invertible portion 42 of the cusp 30. Since invertible portion 42 is flexible, it can deform under the exerted pressure and invert to form another approximate semi-cone, as shown in FIG. 2C. That is, each cusp 30 forming a first semi-cone in the first position can invert or flip relative to a radial axis of vessel 46 to form a second semi-cone that is approximately the mirror image of the first semi-cone. As the interior 32 of the second semi-cone accumulates retrograde flowing fluid, pressure is exerted on the interior of cusp 30, causing the cusp to move away from the wall 44 of the vessel. As a result, the space 53 between the two cusps 30 narrows, the size of opening 50 decreases, and fluid flow through the vessel and past the cusps is reduced (FIG. 4).

The cusps 30 can remain in the second position until antegrade fluid flow exerts sufficient pressure on the surface of cusps 30 opposite interior 32 and inverts the cusps to the first position. Thus, cusps 30 provide an artificial valve that automatically responds to the flow of fluid or pressure changes in vessel 46.

Figure 5A:
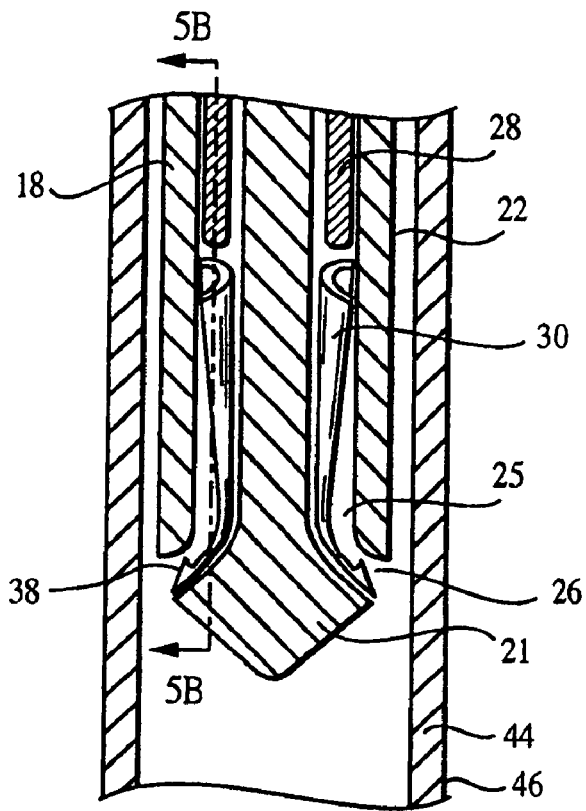
FIGS. 5A, 5B, 5C, 5D and 5E are schematic views of an embodiment of a method for implanting a valve cusp.
Figure 5B:
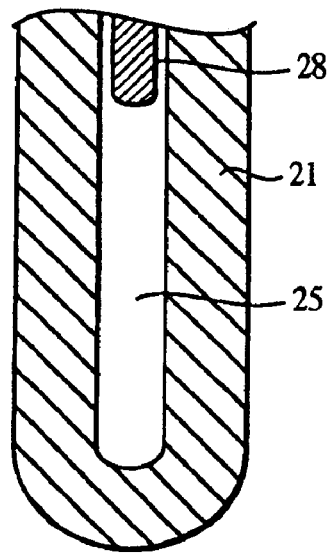

FIGS. 5A to 5E show one method of positioning cusps 30 at a treatment site in vessel 46 using a catheter 18 that may be delivered into the vessel 46 ercutaneously. The catheter 18 is generally adapted for delivery through the vessel 46, e.g., using a guidewire. Catheter 18 includes a long, flexible body having a central portion 21, and a retractable sheath 22 over the central portion. Referring particularly to FIG. 5B, a cross-sectional view of FIG. 5A taken along line 5—5, two grooves 25 are formed on either side of the central portion 21, and a push rod 28 is positioned inside each of the grooves 25. Each cusp 30 is positioned in a groove 25 in a compacted state and held in place by the retractable sheath 22 until delivery at the treatment site.

Figure 5C:
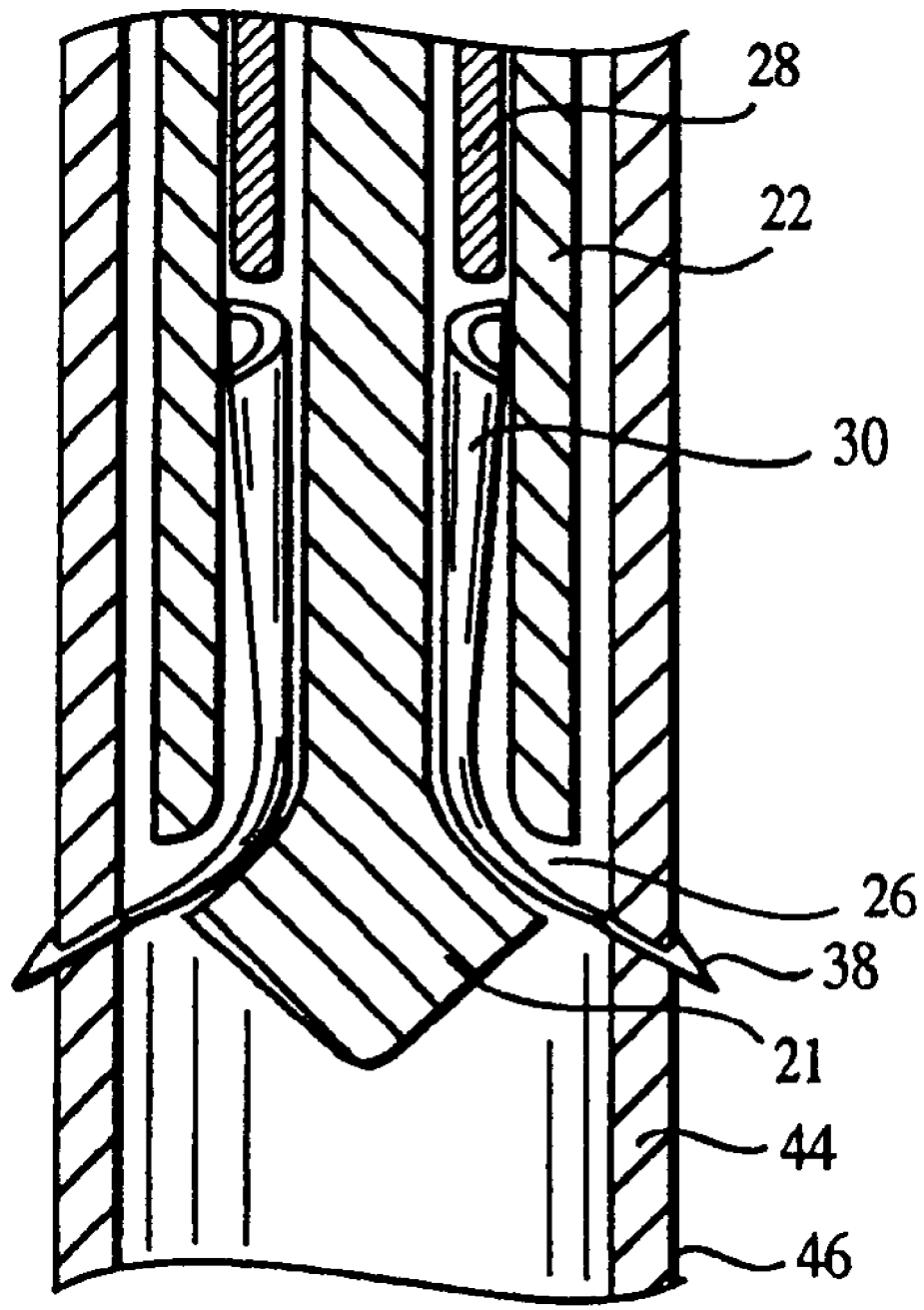

Catheter 18 can be delivered to the treatment site using endoprosthesis delivery techniques, e.g., by tracking an emplaced guidewire with central lumen 101. At the treatment site, the retractable sheath 22 is retracted proximally to form an opening 26 at the end of each groove 25. Referring particularly to FIG. 5C, push rods 28 are used to push each cusp distally toward the opening 26 to push the anchoring element 38 out of the opening 26. The cusps 30 are pushed out of the openings 26 until the anchoring elements 38 secure the cusps 30 to the wall 44 of the vessel 46. For example, the anchoring elements 38 can embed within the wall 44 or penetrate the wall 44 and secure to the exterior of the vessel 46.

Figure 5D:
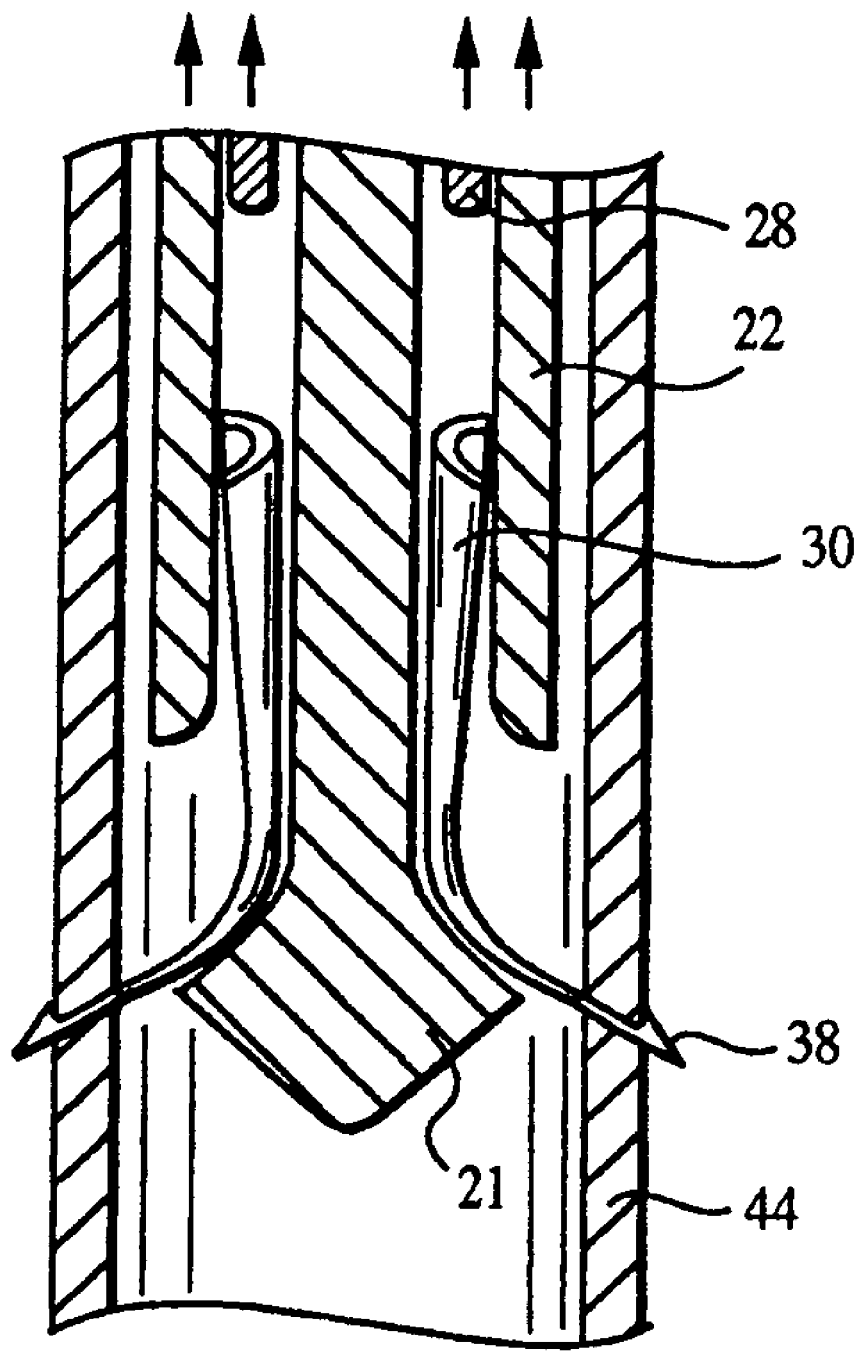
Figure 5E:
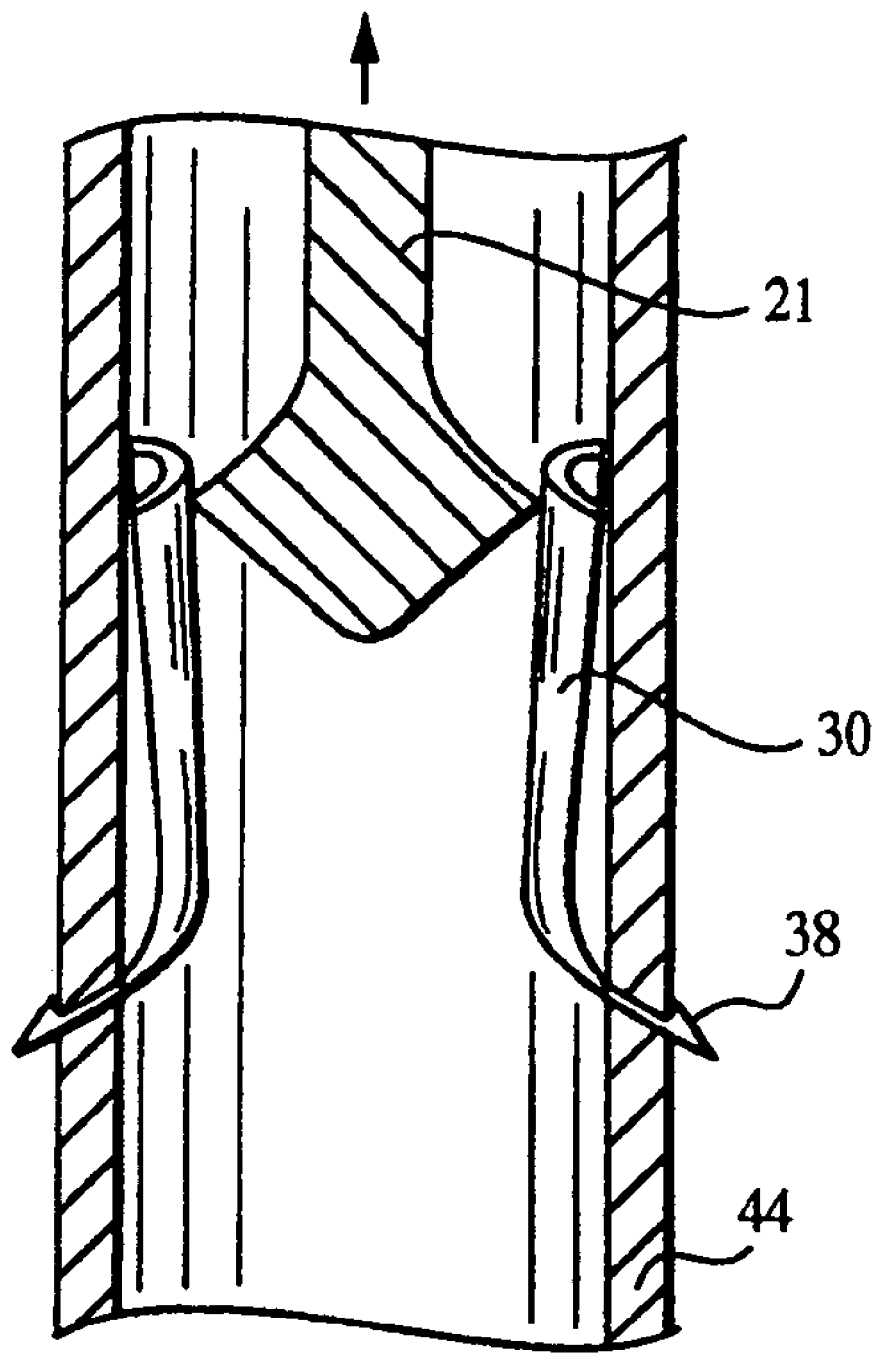

After each cusp 30 is secured to the vessel 46, the retractable sheath 22 is retracted to fully expose the cusps 30 (FIG. 5D). The central portion 21 is then pulled proximally past the flexible (and deflectable) cusps 30 and retracted from the vessel 46 (FIG. 5E). The cusps 30, now secured to the wall 44, can deform between the first and second positions, as described above.

Cusps 30 are preferably made of a biocompatible material capable of reversible deformation as described above. Each cusp 30 can be formed from a thin, flexible material, such as a polyurethane, polyethylene or fluoroplastic, for example, polytetrafluoroethylene (PTFE). Invertible portion 42 can be formed of one or more materials. For example, invertible portion 42 may include an edge portion that is relatively more flexible or more compliant than another portion of the invertible portion to help the edges meet and seal when the cusps 30 are in the second position. Cusps 30 can include a radiopaque material, such as a polymer including a radiopacifier, e.g., tantalum metal or bismuth oxychloride, for positioning and monitoring the cusps.

Similarly, anchoring element 38 is preferably biocompatible. The anchoring element 38 can be formed of a relatively rigid material, such as a polymer having suitable hardness, for example, acrylonitrile-butadiene-styrene (ABS). Other materials can be used, such as metals (e.g., tantalum, tungsten or gold), alloys (e.g., stainless steel or Nitinol), and ceramics. Anchoring elements 38 can include a radiopaque material for positioning and monitoring cusps 30. The anchoring element can be embedded in the invertible portion or fixed to a surface of the invertible portion with, for example, adhesive.

OTHER EMBODIMENTS

Figure 6A:
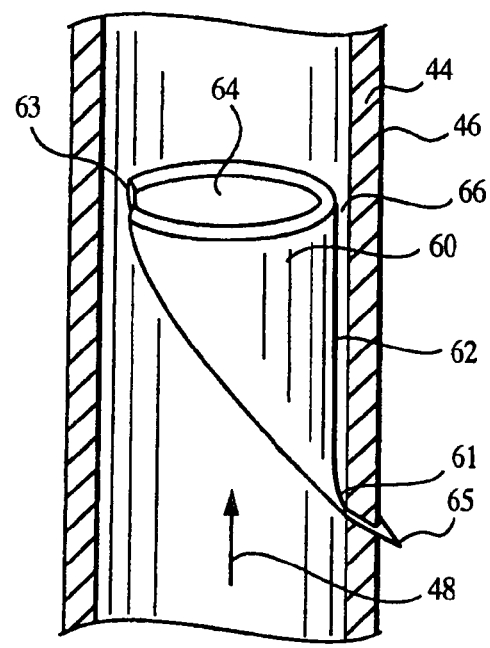
FIGS. 6A and 6B are partial perspective views of an embodiment of a valve cusp.
Figure 6B:
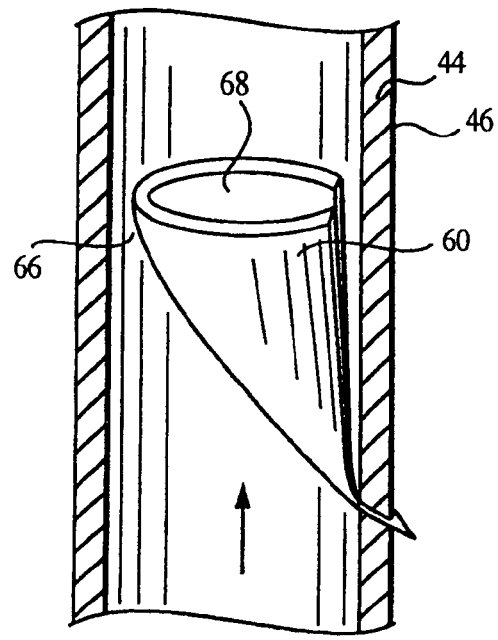

In other embodiments, any number of cusps can be anchored to the wall 44 of the vessel 46 to function as a valve for preventing retrograde flow of blood through the blood vessel 46. Referring to FIGS. 6A and 6B, a single cusp 60 can be used. The cusp 60 can be 10 transported to the treatment site and anchored to the wall 44 of a vessel 46 in the same manner as described above using a catheter. In a first position, the cusp 60 forms an approximate semi-cone, with the edges 63 of the semi-cone facing the wall 44 opposite from where the cusp 60 is anchored to the wall 44. The interior of the cone forms a channel 64 allowing fluid flow past the cusp 60. The anchoring element 65 holds the cusp 30 slightly away from the wall 44 such that a gap 66 is formed between the cusp 60 and the wall 44. Retrograde flowing fluid can accumulate in the gap 66 and exert pressure on the cusp 60, deforming the cusp 60 and widening the gap 66 until the pressure on the cusp 60 inverts the cusp. Referring particularly to FIG. 6B, in an inverted position the cusp 60 forms an approximate cone with the wall 44 and accumulates retrograde flowing fluid in a sack 68 formed by the interior of the cone. Accumulated fluid can exert pressure on the cusp 60, causing the cusp 60 to move away from the wall 44. As a result, the space 66 between the cusp 60 and the wall 44 opposite the anchoring element narrows, until the cusp 60 touches the wall 44, in a second position as shown. In the second position, flow is reduced past the cusp 60 relative to the flow when the cusp 60 was in the first position. The cusp 60 remains in the second position until pressure exerted on the cusp 60 by the antegrade flow of fluid is sufficient to invert the cusp 60 to the first position.

Figure 7A:
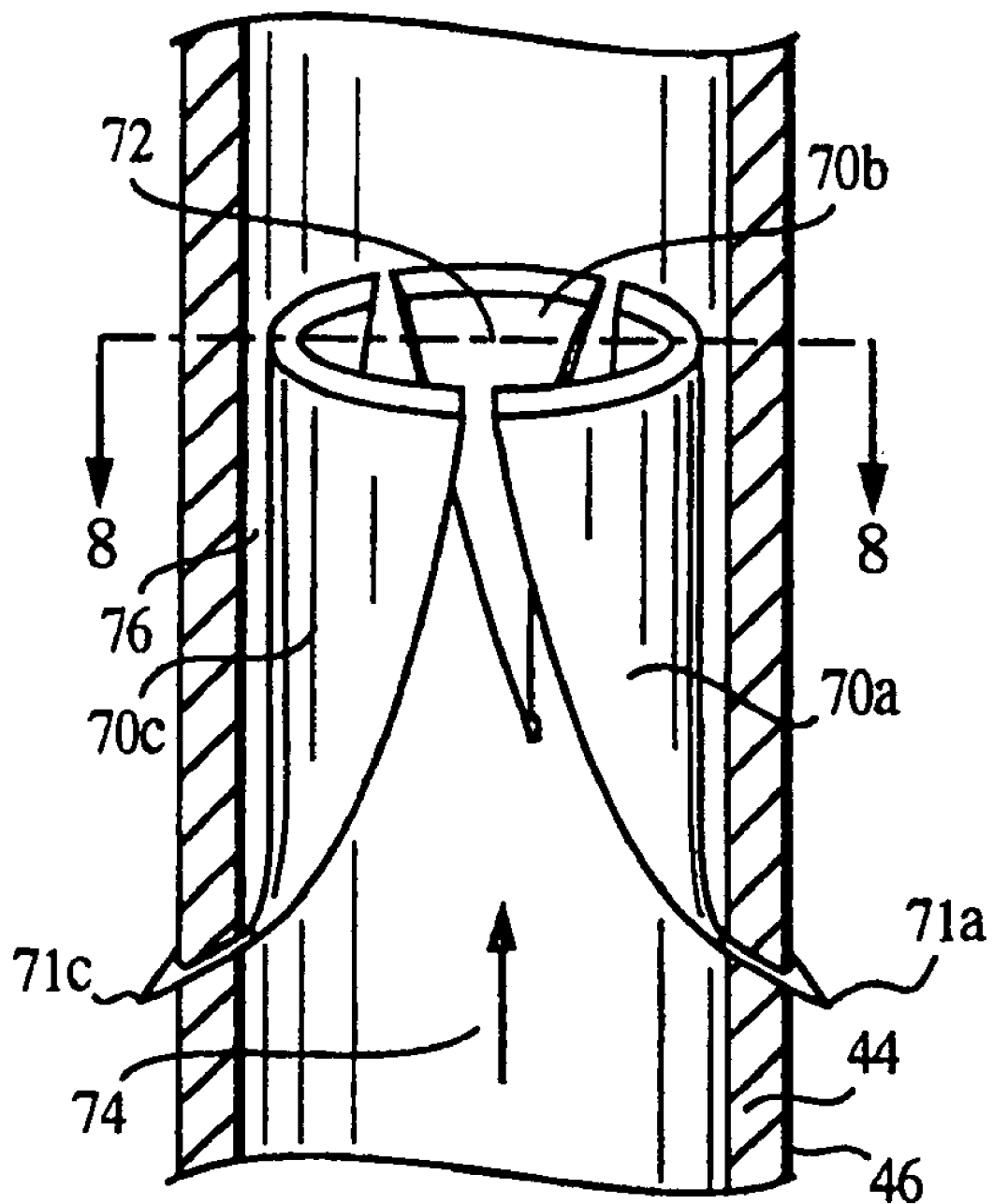
FIGS. 7A and 7B are partial perspective views of an embodiment of a valve cusp.
Figure 7B:
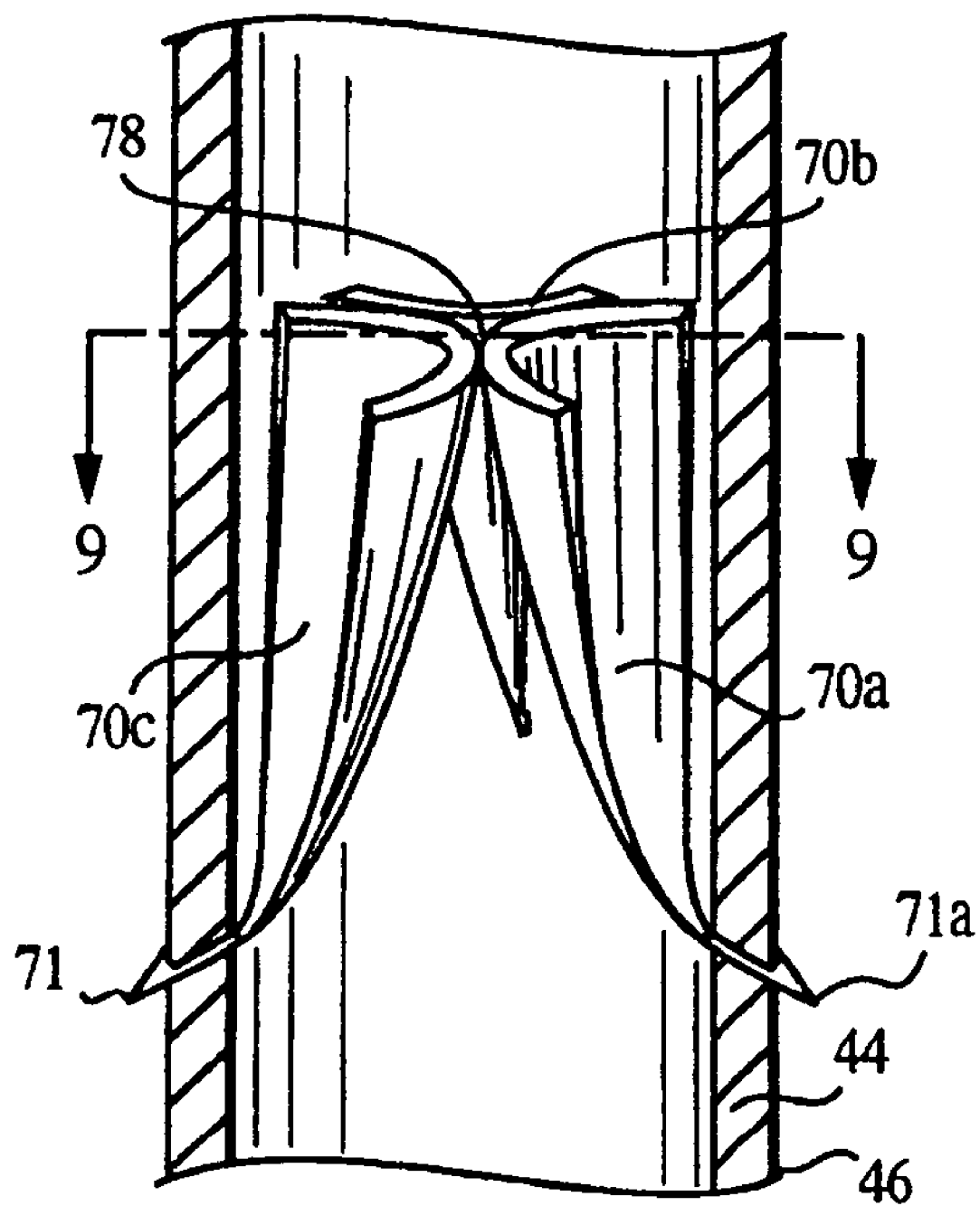
Figure 8:
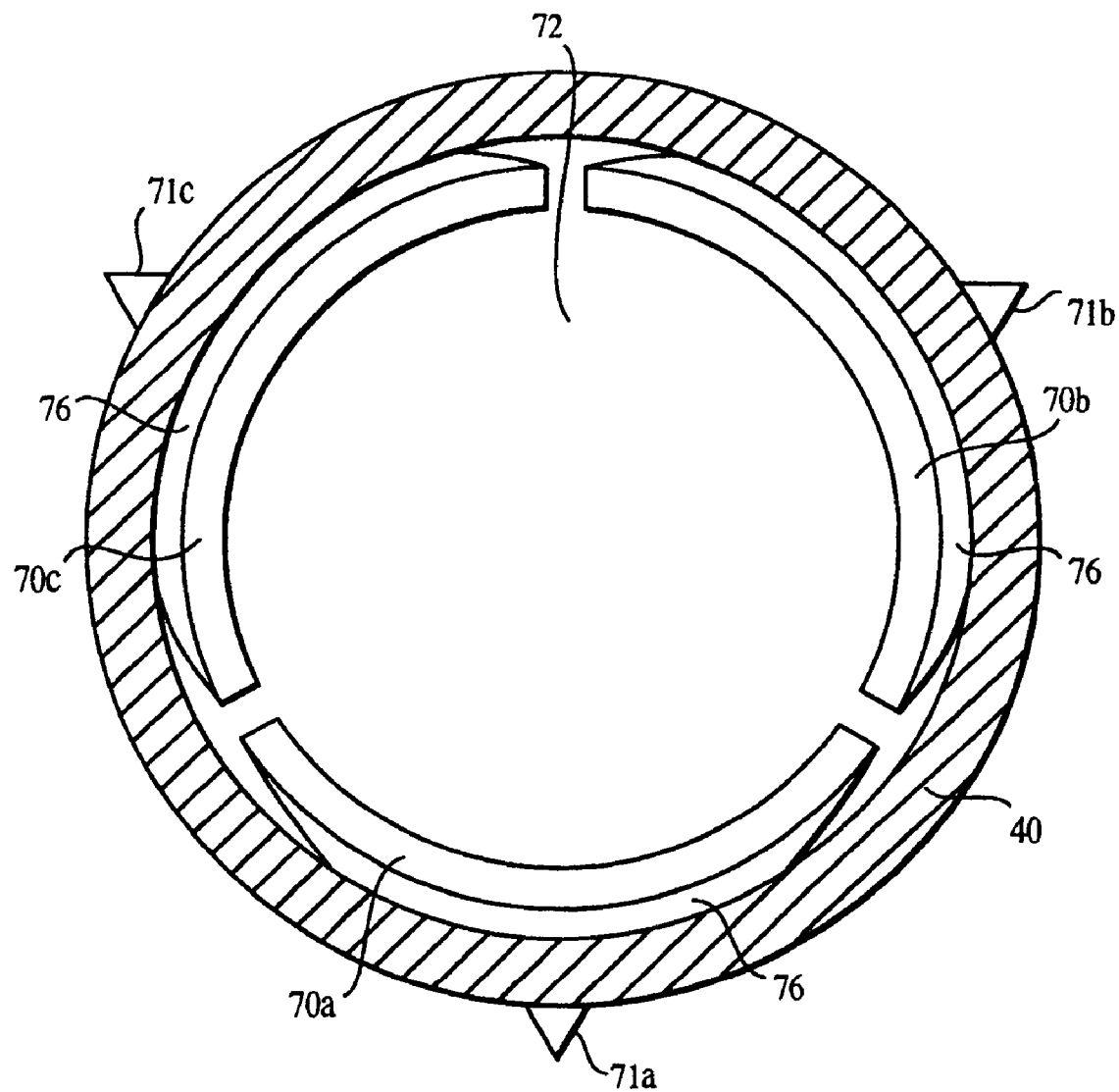
FIG. 8 is a cross-sectional view of the valve cusp of FIG. 7A, taken along line 8—8.

Referring to FIGS. 7A–7B, three cusps 70a–70c can be symmetrically secured to the wall 44 of a vessel 46 in a similar manner as described above. Referring particularly to FIG. 7A, the cusps 70a–70care shown in first position that does not substantially impede flow of a fluid through the vessel 46. As shown in FIG. 8, the surfaces of the cusps 70a–70cconform to the wall 44 of the vessel 46, allowing a substantial opening 72 for flow past the cusps 70a–70c. Each cusp 70a–70cis held away from the wall 44 by anchoring elements 71a–71c, such that a gap 76 is formed between each cusp and the wall 44. As described above, retrograde flowing fluid accumulates in the gap 76 and exerts pressure on the cusp 70, causing the cusp to deform away from the wall 44, until the cusps invert.

Figure 9:
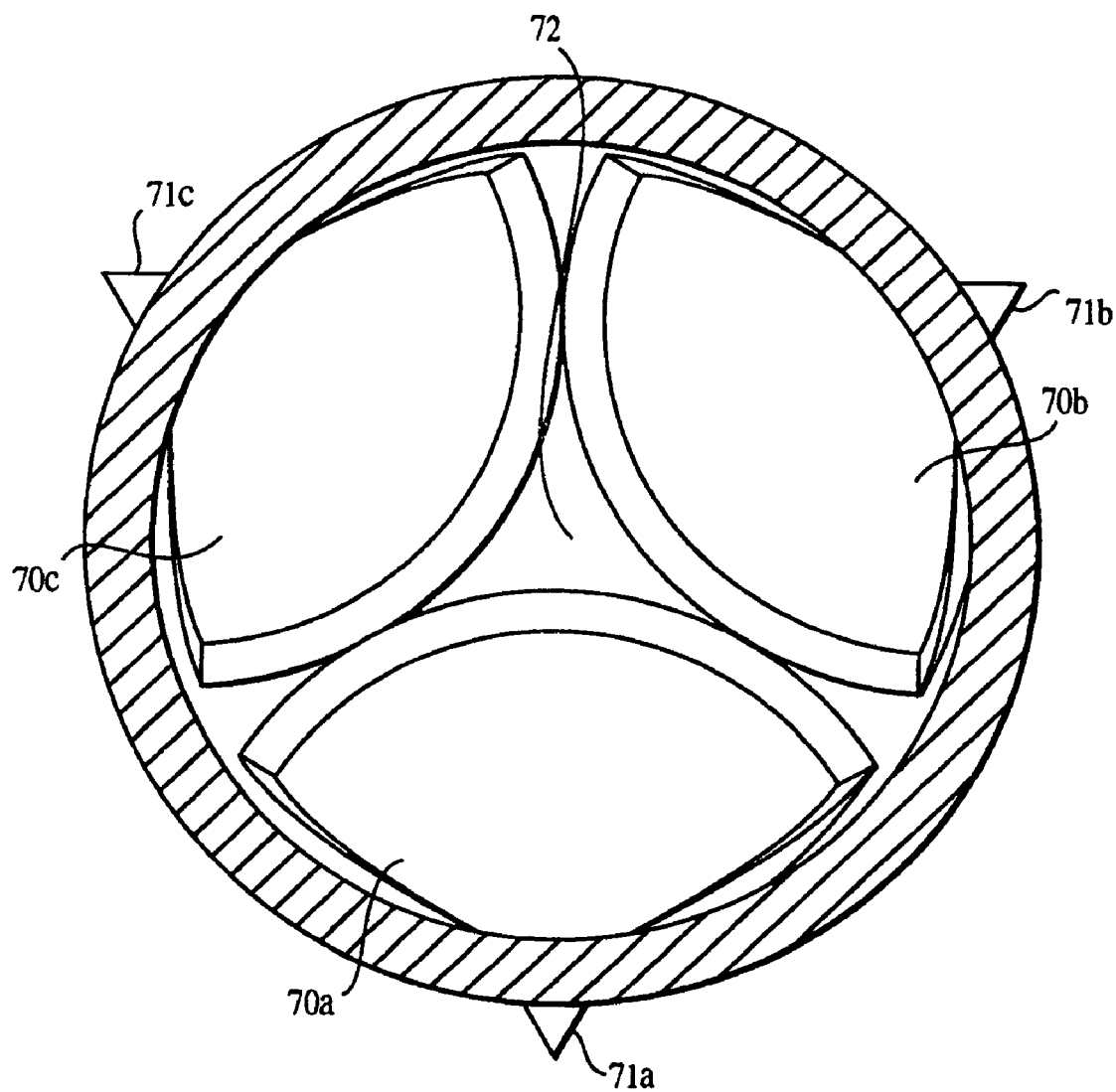
FIG. 9 is a cross-sectional view of the valve cusp of FIG. 7B, taken along line 9—9.

Referring particularly to FIG. 7B, in an inverted position the interior of each cusp 70a–70caccumulates retrograde flowing fluid. Exerting pressure on the cusps causes them to move toward one another, until the cusps 70a–70cmeet in a second position and reduce flow past the cusps 70a–70crelative to the when the cusps 70a–70care in the first position. Referring to FIG. 9, the opening 72 is significantly reduced, thus restricting the fluid flow. The cusps 70a–70cremain in the second position until pressure exerted on the cusps 70a–70cby antegrade flow of fluid inverts the cusps to the first position.

Although the embodiments above describe a device having one to three cusps, any number of cusps can be used to prevent retrograde flow through a vessel. The cusps can be arranged symmetrically as shown, or can be arranged in any other configuration. Although the embodiments described above included cusps of similar size and configuration, cusps of differing sizes and configurations can be used in conjunction with each other.

Figure 10:
FIG. 10 is a partial perspective view of an embodiment of an anchoring element.
Figure 11:
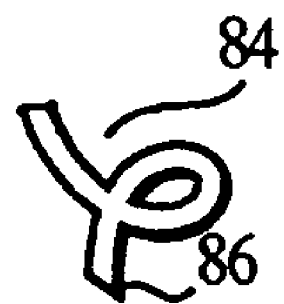
FIG. 11 is a partial perspective view of an embodiment of an anchoring element.

The anchoring element can take a number of different forms that permit the end of the cusp to penetrate the wall of a blood vessel and restrain the end of the cusp from re-entering the vessel. For example, the anchoring element can be a barb element, as shown in the embodiments described above. Alternatively, the anchoring element can be a T-hook device 80 as shown in FIG. 10, wherein T-hook 80 penetrates the wall of a vessel and hooks 82 prevent the anchor from re-entering the vessel. In another embodiment, the anchoring element can define a loop 84, as shown in FIG. 11, wherein the looped end 86 prevents the anchor from re-entering the vessel.

In other embodiments, a cusp can include more than one anchoring element. A cusp can have other polygonal configurations. For example, a generally rectangular cusp can be secured to a vessel using two anchoring elements adjacent to two corners of the cusp. The cusp can form a semi-cylinder.

Other embodiments are within the scope of the following claims.

What is claimed is:

1. A method comprising:
positioning two or more frameless membranes in a body lumen, each membrane invertibly deformable between a first position and a second position,
wherein at least one frameless membrane is invertible in response to the direction of fluid flow through the lumen relative to the membrane in the first position.

2. The method of claim 1, including positioning the two or more frameless membranes symmetrically in the body lumen.

3. The method of claim 1, wherein the two or more frameless membranes include an anchoring element, the method further including:
penetrating the anchoring element through the body lumen.

4. The method of claim 1, wherein the two or more frameless membranes include an anchoring element, the method further including:
embedding the anchoring element of at least one frameless membrane into the body lumen.

5. A medical system, comprising:
a first frameless membrane;
an elongate catheter including a central portion including a first groove surrounded by a retractable sheath, the first frameless membrane positioned in the first groove between the retractable sheath and the central portion; and
a first push rod extending through the elongate catheter to the first groove to contact and extend the first frameless membrane from the elongate catheter.

6. The medical system of claim 5, wherein the first frameless membrane includes an anchoring element, where the first push rod contacts the anchoring element of the first frameless membrane.

7. The medical system of claim 6, wherein the first push rod pushes the anchoring element of the first frameless membrane from an opening of the first groove.

8. The medical system of claim 7, wherein the retractable sheath fully retracts to expose the first frameless membrane.

9. The medical system of claim 5, further including:
a second frameless membrane including an anchoring element, wherein the central portion of the elongate catheter further includes a second groove, the second frameless membrane positioned in the second groove between the retractable sheath and the central portion; and
a second push rod extending through the elongate catheter to the second groove to contact the anchoring element and extend the second frameless membrane from the elongate catheter.

10. The medical system of claim 9, where the first frameless membrane and the second frameless membrane are invertibly deformable between a first position and a second position in response to a direction of a fluid flow past the first frameless membrane and the second frameless membrane.

11. The medical system of claim 9, where each of the first frameless membrane and the second frameless membrane define a portion of a cone.

12. The medical system of claim 11, where each of the first frameless membrane and the second frameless membrane include an anchoring element adjacent to a vertex of the cone.

13. The medical system of claim 12, where the sheath retracts to provide a first opening and a second opening, where the anchoring element of the first frameless membrane is pushed by the first push rod through the first opening, and the anchoring element of the second frameless membrane is pushed by the second push rod through the second opening.

14. The medical system of claim 13, where the anchoring element of the first frameless membrane and the second frameless membrane are formed of a relatively rigid material.

15. The medical system of claim 13, where the anchoring element of the first frameless membrane and the second frameless membrane includes a loop.

16. The medical system of claim 13, where the anchoring element of the first frameless membrane and the second frameless membrane includes a barb.

17. The medical system of claim 9, where the first frameless membrane and the second frameless membrane are formed of a polymer.

18. The medical system of claim 17, where the polymer is a material selected from a group consisting of polyurethanes, polyethylenes, and fluoroplastics.

19. The medical system of claim 9, where the first groove and the second groove are positioned symmetrically in the elongate catheter.

* * * * *